United States Patent [19]

Sato et al.

[11] Patent Number: 4,841,952
[45] Date of Patent: Jun. 27, 1989

[54] ENDOSCOPE WITH AN OPTICAL SYSTEM

[75] Inventors: Michio Sato; Koji Kambara; Yukio Nakajima, all of Tokyo, Japan

[73] Assignee: Olympus Optical Co., Ltd., Tokyo, Japan

[21] Appl. No.: 116,018

[22] Filed: Oct. 30, 1987

[30] Foreign Application Priority Data

Nov. 6, 1986 [JP] Japan ................... 61-170750
Nov. 28, 1986 [JP] Japan ................... 61-183407
Nov. 28, 1986 [JP] Japan ................... 61-183408

[51] Int. Cl.⁴ .............................. A61B 1/00
[52] U.S. Cl. ............................ 128/6; 128/4
[58] Field of Search .......... 128/4, 6; 358/98; 350/96.26

[56] References Cited

U.S. PATENT DOCUMENTS

| 3,583,393 | 6/1971 | Takahashi | 128/4 |
| 3,643,653 | 2/1972 | Takahashi et al. | 128/6 |
| 3,788,304 | 1/1974 | Takahashi | 128/6 |
| 3,946,727 | 3/1976 | Okada et al. | 128/4 |
| 4,279,246 | 7/1981 | Chikama | 128/6 |
| 4,327,711 | 5/1982 | Takagi | 128/4 |

FOREIGN PATENT DOCUMENTS

| D. 3327933A1 | 8/1983 | Fed. Rep. of Germany . | |
| D. 3437228C2 | 10/1984 | Fed. Rep. of Germany . | |
| 4844635 | 12/1968 | Japan . | |
| 5029486 | 7/1973 | Japan . | |
| 5826641 | 6/1978 | Japan . | |
| 5929217 | 8/1982 | Japan . | |
| 0190914 | 11/1983 | Japan | 358/98 |
| 0118711 | 6/1986 | Japan | 350/96.26 |

Primary Examiner—Leo P. Picard
Assistant Examiner—Jessica J. Harrison
Attorney, Agent, or Firm—Ladas & Parry

[57] ABSTRACT

An endoscope having an control section and an inserting section fitted with an optical system. A tubular lens frame of the optical system is disposed at the head part of the inserting section and an inclined end face which is tapered inward is formed all around the end face of the lens frame. A plurality of optical members are arranged in the lens frame and the inclined end face of the lens frame forms a substantially V-shaped annular groove together with the outside surface of an optical member disposed at the end portion of the lens frame. An adhesive is accumulated first in the annular groove and then filled in the clearance between the optical member and the lens frame. In this way, the optical member is secured airtightly to the lens frame.

5 Claims, 3 Drawing Sheets

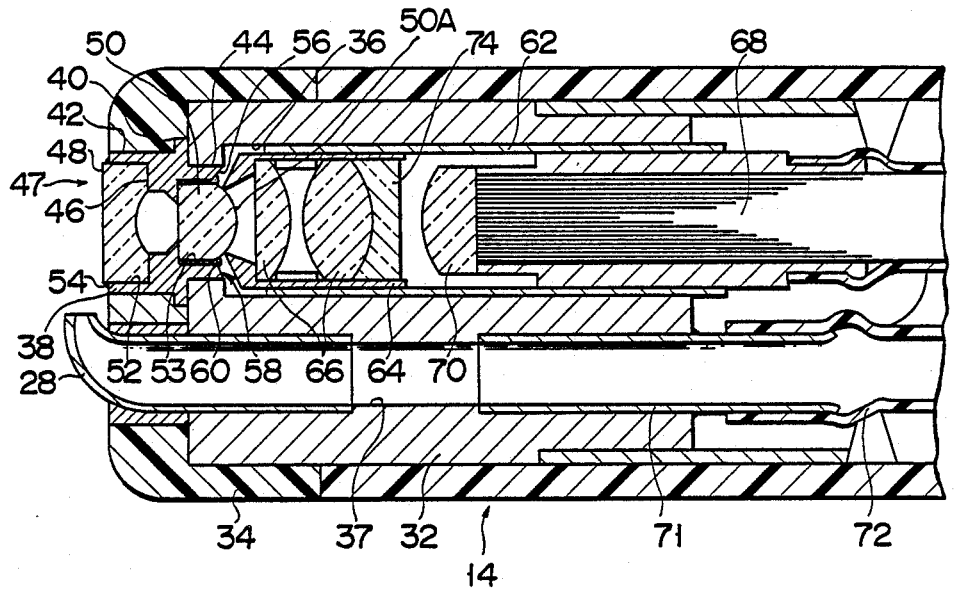
F I G. 1
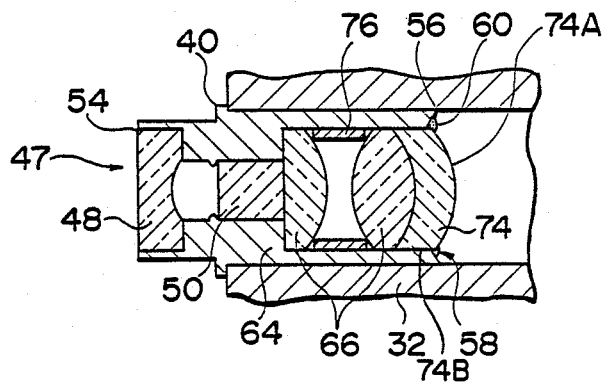
F I G. 2

4,841,952

ENDOSCOPE WITH AN OPTICAL SYSTEM

BACKGROUND OF THE INVENTION

A. Field of the Invention

This invention relates to an endoscope with an improved optical system and a process of manufacturing the optical system.

B. Description of the Prior Art

An objective optical system is fitted in the head part of an insertion section of a typical endoscope. For example, in the conventional endoscope disclosed in Japanese Utility Model Disclosure No. 53-121844, an objective optical system fitted in the head of an insertion section. This optical system comprises a first objective lens placed at the forefront and a group of objective lenses placed at the rear of the first objective lens. The first objective lens is mounted air-tightly on a mount, with its front face exposed. At the rear of the first objective lens, a group of objective lenses other than the first objective lens are mounted on a mount.

A conventional objective optical system has a drawback. When the objective lenses are subjected to rapid changes in temperature, dew condenses on the inside face of a first objective lens, making observation difficult. For example, when the front face of the first objective lens is washed, the lens is cooled rapidly from a temperature near the human body temperature. Water vapor may have entered the internal space of the objective optical system little by little through a covering of the inserting section of the endoscope. If this is the case, the high-temperature humid air around the objective lenses is cooled, and dew condenses on the inside face of the first objective lens, thus clouding the lens.

A technique has been proposed to prevent the clouding of a lens due to condensation of water vapor. In this technique, a first objective lens and a second objective lens are mounted airtightly to a lens frame, thereby airtightly sealing the space between the two objective lenses. Specifically, a first objective lens is set and glued to one end of a lens frame. In this way, the first objective lens is secured airtightly. Then, another lens is inserted into the lens frame through an opening at the other end of the lens frame. The lens frame has an inside diameter a little larger than the diameter of the lenses to be inserted. Finally, a cylindrical clearance between the outer periphery of a lens and the inner periphery of the lens frame is filled with an adhesive.

In the above-described filling of an adhesive to secure the rear lens, since one end of the lens frame has been closed airtightly, it is necessary to fill the clearance with adhesive, to expel the air from the clearance. When adhesive is applied into the clearance, it moves slowly, due to the surface tensions, from the inner periphery of the lens frame and the outer periphery of the lens, thus quickly expelling the air from the clearance. However, when an adhesive is supplied forcedly faster than this air-expelling speed, the air is trapped in the adhesive, inevitably forming many bubbles in the adhesive.

Consequently, when the adhesive hardens and its volume contracts, the air bubbles in the adhesive form pinholes which connect the space, defined by the first objective lens, the rear lens and the lens frame, to the outside, impairing the airtightness of the objective optical system.

Therefore, in filling an adhesive in assemblying objective optical systems, skilled labor is required to fill adhesive in the clearance at a speed lower than the air-expelling speed. In addition, many workhours is required.

SUMMARY OF THE INVENTION

An object of this invention is to provide a process of manufacturing an optical system, wherein a lens frame and optical members can be easily connected in a short time.

Another object of this invention is to provide an endoscope provided with the above-mentioned optical system.

According to the invention, there is provided an endoscope which comprises an insertion section having a control section and another insertion section having an optical system. A tubular lens frame is provided at the distal end portion of the insertion section. An inclined end face tapered inward is formed all around the end face of the lens frame. A plurality of optical members which constitute the optical system are arranged in the lens frame. A substantially V-shaped annular groove is formed by the inclined end face of the lens frame and outside surfaces of the optical member arranged at the end portion of the lens frame. The V-groove is first filled with an adhesive, which then goes into and fills a gap formed between the optical members and the lens frame, thereby securing the optical members to the lens frame.

Further, according to the present invention, there is provided a process of manufacturing an optical system comprising the steps as follows. An inclined end face which tapered inward is formed all around the end face of a lens frame. A plurality of optical members are arranged in the lens frame. The inclined end face forms a substantially V-shaped annular groove together with outer surfaces of the optical member at the end portion of the lens frame. An adhesive first is accumulated in the V-groove, and then caused to gradually fill the gap formed between the optical members and the lens frame, thereby securing the optical members to the lens frame.

Adhesive is applied into the V-groove formed between the sloped part of the lens frame and the outer surfaces of the optical members. It therefore flows slowly into the gap between the lens frame and the optical members. For this reason, a time can be secured which the adhesive requires to expel the air from the gap.

Hence, a lens frame and optical members can be easily bonded together, without forming bubbles in the adhesive. Further, no skilled labor is required, and workhours required can be reduced.

BRIEF DESCRIPTION OF THE DRAWINGS

FIG. 1 is a longitudinal sectional view showing an insertion section of a endoscope according to an embodiment of this invention;

FIG. 2 is a longitudinal sectional view showing a modification of an optical system;

DETAILED DESCRIPTION OF THE PREFERRED EMBODIMENT

An endoscope with an optical system, and a process of manufacturing the optical system, both according to this invention, will now be described with reference to the accompanying drawings.

Figures 3, 4:
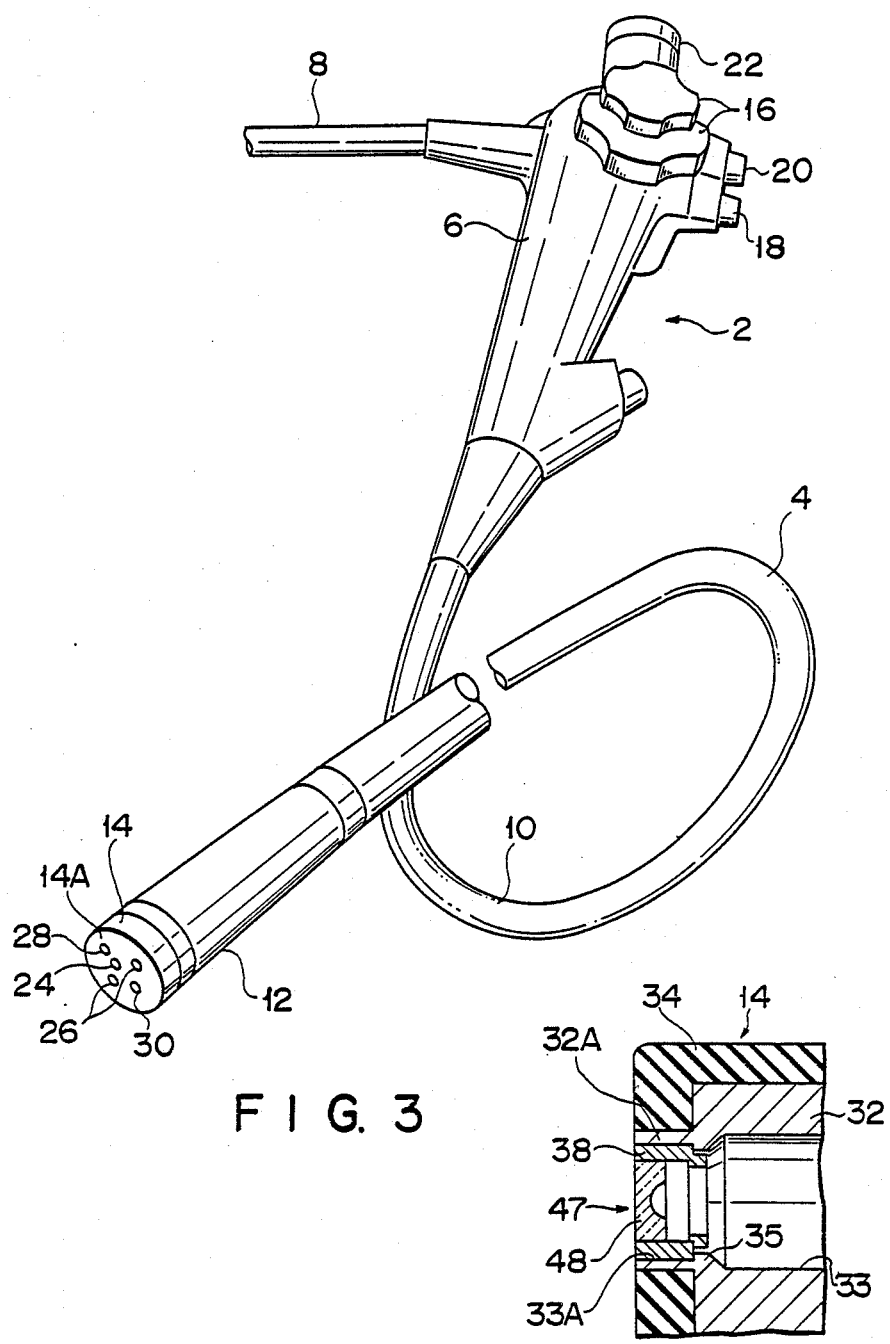
FIG. 3 is a perspective view showing the whole of the endoscope of this invention.
FIG. 4 a fragmentary longitudinal view of a modification of a distal end portion of the endoscope.

FIG. 3 shows a general view of an endoscope as an embodied example of this invention. Endoscope 2 comprises insertion section 4 which is inserted into the abdominal cavity, operating section 6 to manipulate a working section of the endoscope and light guide cable 8 connected to a light source unit (not shown). Insertion section 4 is composed of flexible portion 10 connected to operating section 6 and bending portion 12 and distal end portion 14 both connected to the distal end of flexible portion 10. Operating section 6 is composed of eyepiece 22 for observation, air/water supply button 18 to drive an air/water supply unit (not shown), suction button 20 to drive a suction unit (not shown) and angle knob 16. Angle knob 16 is used to bend bending portion 12 to a desired direction. Distal end portion 14 is provided at its front end with observation port 24 connected to eyepiece 22, a couple of lighting ports 26 connected to light guide cable 8, nozzle 28 connected to the air/water supply unit and suction port 30 connected to the suction unit.

Referring to FIG. 1, distal end portion 14 has housing 32 and the front end of housing 32 is covered with head cover 34. Housing 32 and head cover 34 have through hole 36 bored in the longitudinal direction of insertion section 4. Tubular lens frame 38 is fitted into the front end portion of through hole 36 and the fitted surface is sealed. Lens frame 38 has ring-like projection 40 around the circumference in the middle portion of lens frame 38 and also has large-diameter cylindrical part 42 before and small-diameter cylindrical part 44 after the ring-like projection 40. Between cylindrical parts 42 and 44 there is internal ring-like projection 46. Fitted in first mounting hole 52 of large-diameter part 42 of lens frame 38 is a first objective lens 48 which is an optical member of optical system 47. Fitted in second mounting hole 53 of small-diameter part 44 is a second objective lens which is another optical member and has spherical lens face 50A facing backward.

The inside diameter of first mounting hole 52 of large-diameter part 42 is a little larger than the outside diameter of first objective lens 48. The clearance between mounting hole 52 and lens 48 is filled with adhesive 54 with no void space left, thereby ensuring the airtightness of the lens frame 38.

The inside diameter of second mounting hole 53 of small-diameter cylindrical part 44 into which second objective lens 50 is mounted is a little larger than the outside diameter of second objective lens 50. Around the end face of small-diameter cylindrical part 44, substantially V-shaped annular groove 58 is formed by inclined end face 56 tapered inward all around the end face of small-diameter cylindrical part 44, an exposed lateral circumferential surface of second objective lens 50 and a peripheral area of face 50A.

With optical system 47 of the endoscope of this invention, V-shaped groove 58 formed as mentioned above is first filled with adhesive 60, then the cylindrical clearance, formed between second objective lens 50 and lens frame 38, is filled with adhesive 60 with no void space left, thereby securing second objective lens 50 to lens frame 38. Hence, the airtightness in lens frame 38 can be kept securely.

Supporting cylinder 62 for mounting other optical members is fitted into the rear part of through hole 36 and second lens frame 64 incorporating rear group of lenses 66 is fitted into the front part of supporting cylinder 62. Inserted and secured to the rear part of supporting cylinder 62 are image guide fibers 68. To the front end of image guide fibers 68, lens 70 is attached.

Nozzle 28 for supply of air and water is mounted at the front part of second through hole 37 of housing 32. Through hole 37 is at its rear part fitted with connection tube 71 which is connected with air/water supply tube 72.

A process of manufacturing an optical system of the endoscope according to this invention will now be described in the following. First of all, first objective lens 48 is mounted and glued to first mounting hole 52 of lens frame 38 and thereby secured airtightly. Then, second objective lens 50 is inserted into second mounting hole 53 of lens frame 38. As a result, substantially V-shaped annular groove 58 is formed at the end of small-diameter cylindrical part 44. Adhesive 60 is supplied and accumulated in V-groove 58, and flows from V-groove 58 into the clearance between objective lens 50 and lens frame 38, so slowly that the air is expelled from V-groove 58, that is, at a speed lower than the speed of expelling the air. Thus, the clearance is filled completely, leaving no void space. The air is expelled smoothly from groove 58 by adhesive 60, and is not trapped in adhesive 60 to form bubbles therein.

Therefore, by the process of manufacturing the optical system according to this invention, lens frame 38 and second objective lens 50 can be glued and secured airtightly by a simple work of accumulating adhesive 60 in V-groove 58. Furthermore, the need for skilled work such as assembly of an optical system which used to be necessary has been eliminated and workhours required have been reduced.

By increasing the tilted angle of inclined face 56 by extending the length of the side wall of small-diameter cylindrical part 44, the area of contact between small-diameter cylindrical part 44 and housing 32 can be enlarged, thereby the bonding strength of lens frame can be increased. Therefore, even if an external force is applied to the distal end portion of inserting section 4, the airtight bonding of housing 32 with lens frame 38 cannot be broken easily and troubles such as entry of water into distal end portion 14 can be prevented.

A modification of the optical system according to this invention will now be described with reference to FIG. 2. As for the members already described in the first embodiment of this invention, the same numbers will be used and description of them will be omitted.

In the optical system of this modification, first objective lens 48, second objective lens 50 and rear group of lenses 66 are mounted in lens frame 64. More specifically, first objective lens 48 is mounted air-tightly to lens frame 64 and the innermost lens 74 of the rear group of lenses 66 is mounted to the inside of the rear end portion of lens frame 64. Inclined face 56 is formed all around the rear end face of lens frame 64. V-groove 58 is defined by inclined face 56, the lateral circumferential surface of lens 74 and the peripheral area of lens face 74A of lens 74. V-groove 58 is filled with adhesive 60. Objective lenses 66, which are arranged between first objective lens 48 and innermost lens 74, are separated for a specified distance by means of spacing ring 76. The spaces between the lenses are kept airtight from the outside.

In the first embodiment and the modification described above, a substantially V-shaped annular groove is formed by the inclined face at the end face of the lens frame, the lateral circumferential surface of the lens and the peripheral area of the lens face, but the V-groove may be formed by the inclined face at the end face of the lens frame and the peripheral area of the lens face.

A modification of the distal end portion of the endoscope according to this invention will now be described with reference to FIG. 4.

In this modification, as shown in FIG. 4, distal end portion 14 has housing 32 made of a metal, for example, and formed inside housing 32 is a first internal hole 33 for mounting objective lenses. At the front end of housing 33, cylindrical wall 32A is formed. Formed inside cylindrical wall 32A is a second internal hole 33A for mounting lens frame 38. Cylindrical lens frame 38 is fixed to the second internal hole 33A and first objective lens 48 is glued and secured to the inside of lens frame 38.

The second internal hole 33A communicates with first internal hole 33 via internal projection 35 provided at the front end of housing 32. In cylindrical wall 32A, lens frame 38 is mounted which as a whole is located at the front end of housing 32. The external circumferential surface of lens frame 38 and the internal circumferential surface of cylindrical wall 32A are bonded by an adhesive. The exposed area of housing 32 from its external circumferential surface to its front end is covered with a head cover, more precisely, insulating cover 34. Insulating cover 34 is formed of a insulating rubber, for example, and is glued and secured to housing 32. In this way, the front part of housing 32 is electrically insulated.

In this modification, when an impact is applied to distal end portion 14, the impact given to insulating cover 34 is absorbed by cylindrical wall 32A having sufficient strength and is not transmitted to lens frame 38. Thus, the objective lenses mounted in lens frame 38 are protected from impacts.

Therefore, when the endoscope is operated, even if the distal end portion is subjected to an impact, the bonded layers at portion 14 are not broken and there is no possibility that water enters housing 32. In addition, insulating cover 34 ensures electrical safety.

In this modification, cylindrical wall 32A is integral with housing 32, but these two members may be separate and connected together so long as strength almost equivalent to that of the integral structure can be secured. Needless to say, the structure of housing 32 in this modification can be applied to optical systems other than the objective optical system.

The structure of the inserting section of the endoscope according to this invention will now be described with reference to FIGS. 5 and 6.

Figure 5:
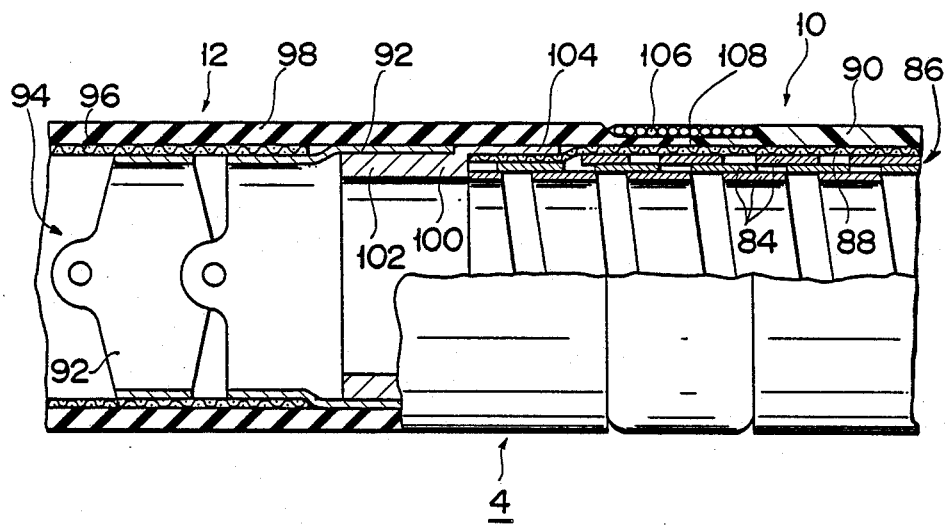
FIG. 5 is a partially cutaway side view showing the insertion section of the endoscope according to the embodiment of this invention.

Inserting section 4 shown in FIG. 5 comprises flexible portion 10, bending portion 12 and distal end portion 14 connected continuously to control section 6. Bending portion 12 is bent by remotely controlling with ankle knob 16 provided at control section 6.

As shown in FIG. 5, flexible portion 10 has reinforcing member 86 consisting of a plurality of spiral tubes 84 made up of spiral-formed metal band plate. This reinforcing member 86 is covered with net tube 88, which is coated with finishing resin 90. Bending portion 12 has reinforcing member 94 consisting of a plurality of tubular segments 92 for bending which are arranged in the longitudinal direction and connected consecutively. Reinforcing member 94 is covered with net tube 96. Flexible portion 10 and bending portion 12 are coupled by means of coupling member 100. To be more specific, coupling member 100 is in a cylindrical form as shown in FIG. 5 and small-diameter part 102 at the front end of coupling member 100 is tightly fitted to rearmost segment 92. Coupling member 100 has connecting part 104 formed at its rear end portion. Connecting part 104 has in its inside reinforcing member 86 of flexible portion 10 and the front end of net tube 88 inserted and secured by bonding, soldering or brazing. The outermost layer of spiral tubes 84 which is positioned within connecting part 104 of coupling member 100 has been removed. As a result, spiral tubes 84 within this connecting part 104 consist of two layers of spiral tubes, whereas spiral tubes 84 outside connecting part 10 consist of three layers of spiral tubes 84. Put otherwise, spiral tubes 84 within connecting part 10 are thinner by on layer of spiral tube 84.

The rear end face of rubber coating 98 of bending portion 12 extends over the front end of flexible portion 10 and butts on the front end face of resin coating 90 of the front part of flexible portion 10. The rear end portion of rubber coating 98 and the front end portion of resin coating 90 are wound with fastening string 106 and fixed with adhesive 108.

As described above, at the connected part of reinforcing member 86 to coupling member 100, the outermost spiral tube 84 has been removed. This makes it possible to give a smaller diameter to connecting part 104 of coupling member 100 proportionately. Therefore, it is also possible to make the outside diameter of the portion where net tube 88 is applied over threefold-superposed spiral tubes 84 equal to the outside diameter of connecting part 104 of coupling member 100. Hence, by applying resin coating 90 and rubber coating 98 of equal thickness, the outside diameters of flexible portion 10 and bending portion 12 can be made identical. Meanwhile, the external circumferential areas of rubber coating 98 and resin coating 90 where fastening string 106 is wound have a recess having a depth equivalent to the thickness of fastening string 106 and adhesive 108.

In inserting section 4 of the endoscope of this invention, as described above, the coupled part of flexible portion 10 with bending portion 12 can be made small in diameter and smooth in external surface. As a result, the patient's pain from use of an endoscope can be alleviated.

Figure 6:
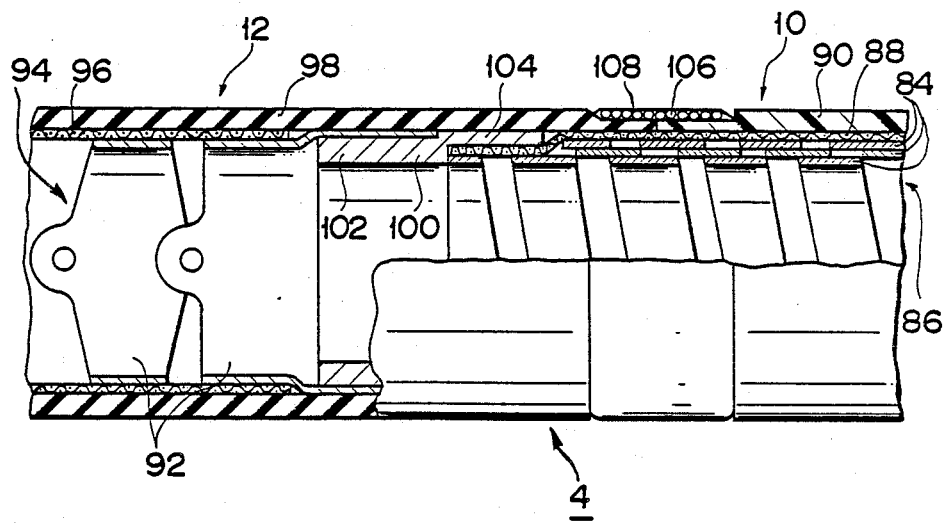
FIG. 6 is a partially cutaway side view showing a modification of the insertion section of the endoscope.

FIG. 6 shows a modification of the insertion section of the endoscope of this invention. In this modification, just as in the first embodiment, threefold-superposed spiral tubes 84 are used to constitute reinforcing member 86 of flexible portion 10. However, at that par of reinforcing member 86 which is fitted into connecting part 104 of coupling member 100, two outer spiral tubes 84 have been removed, leaving the innermost spiral tube 84 intact. Compared with the first embodiment, the thickness of connecting part 104 of coupling member 100 has been increased by the amount equivalent to the thickness of one spiral tube 84. Therefore the strength of coupling member 100, that is, the strength of the connected part can be increased.

Meanwhile, when threefold spiral tubes are used, for example, to constitute reinforcing member 86 of flexible portion 10, even if the middle spiral tube is removed, the same advantage as in the first embodiment can be obtained.

What is claimed is:

1. An endoscope having an operation section and an insertion section containing an optical system, said endoscope comprising:
   a tubular lens frame provided with a distal end portion of said insertion section and having an end face inclined to the axis of the lens frame;
   a plurality of optical members arranged in said lens frame, one of said optical members partly projecting from the end face of said lens frame, which includes a convex lens having a spherical face and a cylindrical body, thus a substantially V-shaped annular groove being defined by the inclined end face of said lens frame and the external circumferential surface of said body; and
   adhesive filled in a gap between said optical member and said lens frame.

2. The endoscope according to claim 1, further comprising:
   a housing disposed at the distal end portion of said insertion section, said housing having a cylindrical projection, into which said lens frame is fitted; and
   an insulating member covering the outside surface of said housing.

3. The endoscope according to claim 1, wherein said insertion section has a bending portion which is bent by manipulating said operation section and a flexible portion connected to said bending portion by means of a coupling member, said flexible portion having a reinforcing member consisting of a plurality of spiral tubes superposed radially, at least the outermost one of said spiral tubes is removed at the connected part of said reinforcing member disposed inside said coupling member.

4. The endoscope according to claim 1, wherein said optical members are secured air tightly to said lens frame by accumulating the adhesive in said annular groove in advance and then having said adhesive gradually filled in the gap formed between said optical members and said lens frame.

5. An endoscope comprising:
   an operation section and an insertion section containing an optical system, said insertion section having a bending portion which is bent by manipulating said operation section and a flexible portion connected to said bending portion by means of a coupling member, said flexible portion having a reinforcing member consisting of a plurality of spiral tubes superposed radially, at least the outermost one of said spiral tubes is removed at the connected part of said reinforcing member disposed inside said coupling member;
   a tubular lens frame provided within a distal end portion of said insertion section and having an end face inclined to the axis of the lens frame;
   a plurality of optical members arranged in said lens frame, one of said optical members partly projecting from the end face of said lens frame, thus defining a substantial V-shaped annular groove together with the inclined end face of said lens frame; and
   adhesive filled in a gap between said optical member and said lens frame.

* * * * *

UNITED STATES PATENT AND TRADEMARK OFFICE
CERTIFICATE OF CORRECTION

PATENT NO. : 4,841,952

DATED : June 27, 1989

INVENTOR(S) : SATO et al

It is certified that error appears in the above-identified patent and that said Letters Patent is hereby corrected as shown below:

Title Page  Column 1, Item [30] which reads:

"61-170750" should read -- 61-170750(U) --

"61-183407" should read -- 61-183407(U) --

"61-183408" should read -- 61-183408(U) --

Signed and Sealed this

Eleventh Day of September, 1990

Attest:

HARRY F. MANBECK, JR.

*Attesting Officer*  *Commissioner of Patents and Trademarks*